United States Patent
Maa et al.

(10) Patent No.: US 12,359,799 B2
(45) Date of Patent: Jul. 15, 2025

(54) LIGHTING APPARATUS WITH NEAR-INFRARED

(71) Applicant: Aleddra Inc., Renton, WA (US)

(72) Inventors: Chia-Yiu Maa, Bellevue, WA (US); Chun-Te Yu, Bellevue, WA (US)

(73) Assignee: Aleddra Inc., Renton, WA (US)

( * ) Notice: Subject to any disclaimer, the term of this patent is extended or adjusted under 35 U.S.C. 154(b) by 282 days.

(21) Appl. No.: 18/209,741

(22) Filed: Jun. 14, 2023

(65) Prior Publication Data
US 2023/0324035 A1 Oct. 12, 2023

Related U.S. Application Data

(63) Continuation-in-part of application No. 18/129,027, filed on Mar. 30, 2023, now Pat. No. 12,251,572, which is a continuation-in-part of application No. 18/101,569, filed on Jan. 25, 2023, now Pat. No. 12,127,314, which is a continuation-in-part of
(Continued)

(51) Int. Cl.
*F21V 23/00* (2015.01)
*F21Y 113/10* (2016.01)
*F21Y 115/10* (2016.01)

(52) U.S. Cl.
CPC ......... *F21V 23/003* (2013.01); *F21Y 2113/10* (2016.08); *F21Y 2115/10* (2016.08)

(58) Field of Classification Search
CPC ... A61N 2005/0659; F21K 9/64; F21K 9/232; F21K 9/23; F21K 9/238; F21K 9/61; F21K 9/235; F21K 9/60; F21K 9/20; F21K 9/65; F21K 9/90; F21K 9/00; F21K 9/62; H05B 45/20; H05B 47/16; H05B 47/11; H05B 47/105; H05B 47/155; H05B 45/31; H05B 45/28; H05B 45/22; H05B 45/00; H05B 45/325; H05B 45/395; H05B 45/46; H05B 47/10; H05B 47/18; H05B 47/184; A61B 1/0684; A61L 2/0047; A61L 2/0052; A61L 2/084; A61L 2/10; A61L 2/24; A61L 2202/11; A61L 2202/14; A61L 2209/111;
(Continued)

(56) References Cited

U.S. PATENT DOCUMENTS

2013/0120688 A1\* 5/2013 Chao .................. G02F 1/133609
  362/277
2020/0333312 A1\* 10/2020 Islam ................... G01N 33/442

FOREIGN PATENT DOCUMENTS

CN 111542370 A \* 8/2020 ............... A61N 5/06

\* cited by examiner

*Primary Examiner* — Monica C King
(74) *Attorney, Agent, or Firm* — Andy M. Han; Han IP PLLC

(57) ABSTRACT

A lighting apparatus includes a first visible light source, a near-infrared (near-IR) radiation source, and a controller. The first visible light source emits a light with a color temperature between 1900K to 6800K, and the near-IR radiation source emitting a wavelength in the 700 nm to 1400 nm wavelength range, and in some cases, with at least 300 nm continuous spectral range of emission between 700 nm to 1400 nm. The radiation energy emitted by the lighting apparatus in the 700 nm to 1400 nm wavelength range is less than the radiation energy emitted by the lighting apparatus in the 380 nm to 700 nm wavelength range. In some embodiments, the controller is configured to strobe the first visible light source with a strobing frequency between 35 Hz and 45 Hz via either an amplitude modulation strobing or a color temperature fusion strobing.

17 Claims, 2 Drawing Sheets

Related U.S. Application Data application No. 17/981,123, filed on Nov. 4, 2022, now Pat. No. 12,048,078, which is a continuation-in-part of application No. 17/509,877, filed on Oct. 25, 2021, now abandoned, which is a continuation-in-part of application No. 17/148,277, filed on Jan. 13, 2021, now Pat. No. 11,191,863, which is a continuation-in-part of application No. 17/094,567, filed on Nov. 10, 2020, now Pat. No. 11,103,612, which is a continuation-in-part of application No. 16/180,416, filed on Nov. 5, 2018, now Pat. No. 10,874,762.

(58) Field of Classification Search
CPC ..... A61L 9/18; A61L 9/20; A61L 2/08; A61L 2202/25; F21Y 2115/10
See application file for complete search history.

LIGHTING APPARATUS WITH NEAR-INFRARED

The present disclosure is a continuation-in-part (CIP) of U.S. patent application Ser. No. 18/129,027, filed 30 Mar. 2023. Content of aforementioned application is herein incorporated by reference in its entirety.

BACKGROUND

Technical Field

The present disclosure pertains to the field of lighting apparatus and, more specifically, proposes a lighting apparatus with near-infrared (near-IR).

Description of Related Art

In U.S. patent application Ser. No. 18/129,027, a therapeutic lighting apparatus was introduced to strobe between two light sources each with a different color temperature at a frequency between 35 Hz and 45 Hz for treating Alzheimer's patients. Some embodiments further include a near-infrared (near-IR) radiation source configured to emit an IR light at a wavelength in a range of 760 nm~1400 nnm such that under a near-IR mode, the near-IR radiation source is turned on for emitting a near-IR wavelength for boosting the general health of a human subject, e.g., lowering the heartbeat, uplifting the mood, and improving the immunization system of the human subject. Under these embodiments, an 850 nm light emitting diode (LED) radiation source with a narrow near-IR wavelength band peaked at 850 nm would meet the requirements. However, recent studies show that the human body responds positively to a wide range of near-IR wavelengths. While the wavelengths from a narrow near-IR band could provide positive stimulation to the human body, it is far more effective and critical to expose the human body with the wavelengths from a broader near-IR band, ideally from a continuous near-IR wavelength range. This is because each near-IR wavelength counts. The present disclosure proposes a lighting apparatus with a broadband near-IR wavelength band for maximizing the near-IR wavelength stimulation of a human subject.

SUMMARY

In one aspect, the lighting apparatus comprises a first visible light source emitting a light with a first color temperature between 1900K to 6800K, a near-IR radiation source emitting a wavelength in the 700 nm to 1400 nm wavelength range, and a controller. The controller is configured to convert an external AC mains power to a first internal power to drive the first visible light source, and the controller is also configured to convert the external AC mains power to a second internal power, different from the first internal power, to drive the near-IR radiation source. Moreover, the controller is configured to set the radiation energy emitted by the lighting apparatus in the 700 nm to 1400 nm wavelength range to be less than the radiation energy emitted by the lighting apparatus in 380 nm to 700 nm wavelength range. It is noted that the first visible light source may emit radiation energy in the 700 nm to 1400 nm wavelength range, and similarly, the near-IR radiation source may emit radiation energy in the 380 nm to 700 nm wavelength range. The present disclosure requires that the lighting apparatus, after combing the radiation energy of the first visible light source and of the near-IR radiation source, emits a lesser radiation energy in the 700 nm to 1400 nm wavelength range than in the 380 nm to 700 nm wavelength range. This technical feature emulates the spectrum power distribution (SPD) of sunlight which has a lower radiation energy in the 700 nm to 1400 nm wavelength range than in the 380 nm to 700 nm wavelength range. More importantly, this technical feature sets the upper limit on the near-IR radiation energy emitted by the lighting apparatus to be always below the visible light radiation energy emitted by the lighting apparatus. By using the visible light radiation energy as the upper limit, a human subject could feel the discomfort of the overly bright visible light before being overly exposed to near-IR radiation, thus triggering the human subject to turn off or turn down or turn away from the lighting apparatus and avoiding being harmed by near-IR radiation overdosage.

There are no restrictions on the form factor of this lighting apparatus. The lighting apparatus may be in the form of a luminaire or a portable electronic device. In some cases, the first visible light source and the near-IR radiation source are not housed in the same housing.

In some embodiments, the near-IR radiation source emits a 300 nm continuous spectral range of emission between 700 nm to 1400 nm. The present disclosure overcomes the deficiency of general indoor lighting equipment presently in use that emits little or no near-IR wavelengths, thus depriving a human subject from getting the adequate stimulation from the near-IR wavelengths, as compared to the near-IR wavelengths the human subject could receive when exposed to sunlight. The technical feature on the near-IR radiation source emitting continuous wavelengths in a 300 nm wavelength range between 700 nm to 1400 nm quantifies a broadband near-IR radiation source. Ideally, the near-IR radiation source could emit all wavelengths between 700 nm to 1400 nm, just like sunlight. However, it may be too expensive to create a full spectrum near-IR radiation source covering all wavelengths between 700 nm to 1400 nm. As a compromise, the technical feature on the near-IR radiation source emitting at least 300 nm continuous spectral range of emission between 700 nm to 1400 nm is used. For example, the near-IR radiation source may emit continuous wavelengths between 700 nm to 1000 nm, or 850 nm to 1150 nm, or 900 nm to 1200 nm, etc. The broader the near-IR wavelength range, the better, for it would positively stimulate a human subject across such broader near-IR wavelength range.

For the near-IR radiation source, having a smoother SPD is preferred over having a peaked SPD, for the former could induce a more evenly distributed response from a human subject over a broader near-IR range, as compared to the latter which may induce a peaked, thus unevenly distributed response from a human subject over a narrow near-IR range. As stated earlier that every near-IR wavelength count, so a broader, smoother near-IR SPD is preferred for the near-IR radiation source. Therefore, in some embodiments, the near-IR radiation source has a smooth (i.e., non-peaked) SPD between 700 nm to 1400 nm.

In some embodiments, the controller is configured to set the radiation energy emitted by the lighting apparatus in the 700 nm to 1400 nm wavelength range to be greater than 10% of the radiation energy emitted by the lighting apparatus in the 380 nm to 700 nm wavelength range. This technical feature ensures that the near-IR radiation of the light apparatus is sufficient, effective, and useful, rather than merely decorative.

In some embodiments, the controller is configured to operate the lighting apparatus in a non-near-IR mode by turning on only the first visible light source but not the near-IR radiation source. In other words, these embodiments support a non-near-IR mode operation for reasons such as attaining a better energy efficiency since the power consumption of the near-IR radiation source would lower the overall energy efficiency of the lighting apparatus due to the fact the near-IR wavelengths make no contribution of the visible light efficacy (in terms of lumens per watt).

In some embodiments, the first visible light source comprises an LED, since LED light source is suitable for being turned on/off at a high frequency and at different intensity easily, thus suitable for supporting strobing operation in some embodiments.

In some embodiments, the near-IR radiation source comprises an LED. LED manufacturing technology enables the creation of a broadband near-IR LED (with a 300 nm continuous spectral range of emission between 700 nm to 1400 nm) at a reasonable cost. Alternatively, in some embodiments, the near-IR radiation source comprises a filament LED, which is known to emit a very broad range of near-IR wavelengths. Further in some embodiments, the near-IR radiation source comprises a filament LED.

If the near-IR radiation source also emits visible wavelengths, it could increase the visible light output of the lighting apparatus. However, this may be undesirable for it may complicate the control of the visible light output of the lighting to a target light level (in lumens). To overcome this issue, in some embodiments, the lighting apparatus further comprises an optical high-pass filter with a cutoff wavelength between 700 nm to 800 nm for attenuating visible wavelengths emitted by the near-IR radiation source. This high-pass filter applies only to the near-IR radiation source for removing its visible wavelengths. FIG. 1(a) shows an SPD of a broadband near-IR LED with significant visible light emission and having a smooth, continuous spectral range of emission between 700 nm to 1050 nm. FIG. 1(b) shows the SPD after being filtered by a high-pass optical filter with a cutoff wavelength at 750 nm. After applying such high-pass filter on the near-IR radiation source, all visible wavelengths of the lighting apparatus would come only from the first visible light source, while providing a smooth, continuous spectral range of emission between 750 nm to 1050 nm.

In some embodiments, the controller is configured to strobe the first visible light source with a strobing frequency between 35 Hz and 45 Hz via amplitude modulation on the light output of the first visible light source. With these embodiments, the lighting apparatus may now be used for treating Alzheimer's patients.

In some embodiments, the controller is configured to modulate the amplitude modulation depth percentage on the light output of the first visible light source to be less than 50%. For example, the maximum light output of the first visible light source is 1000 lm. With an amplitude modulation depth percentage at 40%, the light output of the first visible light source would strobe between 600 lm and 1000 lm. Having the amplitude modulation depth percentage on the light output of the first visible light source to be less than 50% has the effect of reducing the visual discomfort of a human subject due to strobing. This could lead to a more acceptable and thus more effective treatment for Alzheimer's patients.

In some embodiments, the controller is configured to support an adjustable amplitude modulation depth percentage on the light output of the first light source. In other words, the amplitude modulation depth is adjustable, thus allowing each user or patient to adjust the amplitude modulation depth based on personal preference and visual tolerance. It is noted that the greater the modulation depth, the more effective the treatment is for an Alzheimer's patient. However, the downside is that with a greater modulation depth, the strobing may become more visible and may lead to visual discomfort for the patient. For elderly people with vision deterioration and prone to Alzheimer's disease, they are less visual sensitive and thus can and should be given a stronger visual strobing stimulation for treating their Alzheimer's disease more effectively. Therefore, it is preferable to support an adjustable modulation depth such that for elderly people with Alzheimer's disease, the modulation depth percentage may be set to a higher level e.g., 30% or higher for a stronger visual stimulation and thus resulting in a more effective Alzheimer treatment. Similarly, for more visual sensitive people or for preventative Alzheimer treatment, the modulation depth percentage may be set to a lower level, e.g., 10%.

In some embodiments, the controller is configured to dim the light output of the first visible light source while maintaining a same amplitude modulation depth percentage. For example, if the maximum light output of the first visible light source is 1000 lm and the amplitude modulation depth percentage to be 20%, so the controller would strobe the light output of the light source between 800 lm and 1000 lm. When the light output is dimmed to 500 lm, the controller would strobe the light output of the light source between 400 lm and 500 lm, maintaining the amplitude modulation depth percentage at 20%.

In some embodiments, the first visible light source is configured to support more than one color temperature. Further in some embodiments, the controller is configured to tune the first visible light source from one color temperature to another color temperature while maintaining a same amplitude modulation depth percentage. For example, the first visible light can be configured to tune between 3000K and 5000K. The controller can be configured to maintain 20% amplitude modulation depth percentage when the color temperature is switched back and forth between 3000K and 5000K.

In some embodiments, the first visible light source further comprises a second visible light source with a second color temperature and a third visible light source with a third color temperature, different from the second color temperature. Further in some embodiments, the controller is configured to strobe between a first linear combination of the second color temperature and the third color temperature and a second, different linear combination of the second color temperature and the third color temperature at a strobing frequency between 35 Hz and 45 Hz while maintaining the same light output for the lighting apparatus during strobing. For example, the second visible light source is a 3000K LED with 1000 lm light output, and the second visible light source is a 5000K LED with 1000 lm light output. A first linear combination may be 60% 3000K LED light output and 40% light 5000K LED light output, resulting in 60%× 3000K+40%×5000K=3800K at 1000 lm. A second linear combination may be 40% 3000K LED light output and 60% 5000K LED light output, resulting in 40%×3000K+60%× 5000K=4200K also at 1000 lm. The controller would strobe the light output between 3800K and 4200K at a strobing frequency between 35 Hz and 45 Hz. Another first linear combination may be 100% 3000K at 1000 lm and another second linear combination may be 100% 5000K at 1000 lm. The controller would then strobe the light output between 3000K and 5000K at a strobing frequency between 35 Hz and 45 Hz.

BRIEF DESCRIPTION OF THE DRAWINGS

The accompanying drawings are included to aid further understanding of the present disclosure and are incorporated in and constitute a part of the present disclosure. The drawings illustrate a select number of embodiments of the present disclosure and, together with the detailed description below, serve to explain the principles of the present disclosure. It is appreciable that the drawings are not necessarily to scale, as some components may be shown to be out of proportion to size in actual implementation in order to clearly illustrate the concept of the present disclosure.

DETAILED DESCRIPTION OF PREFERRED EMBODIMENTS

Overview

Various implementations of the present disclosure and related inventive concepts are described below. It should be acknowledged, however, that the present disclosure is not limited to any particular manner of implementation, and that the various embodiments discussed explicitly herein are primarily for purposes of illustration. For example, the various concepts discussed herein may be suitably implemented in a variety of lighting apparatuses having different form factors.

The present disclosure discloses a lighting apparatus includes a first visible light source, a near-IR radiation source, and a controller. The first visible light source emits a light with a color temperature between 1900K to 6800K, and the near-IR radiation source emitting a wavelength in the 700 nm to 1400 nm wavelength range, and in some cases, with at least 300 nm continuous spectral range of emission between 700 nm to 1400 nm. The radiation energy emitted by the lighting apparatus in the 700 nm to 1400 nm wavelength range is less than the radiation energy emitted by the lighting apparatus in the 380 nm to 700 nm wavelength range. In some embodiments, the controller is configured to strobe the first visible light source with a strobing frequency between 35 Hz and 45 Hz via either an amplitude modulation strobing or a color temperature fusion strobing.

EXAMPLE IMPLEMENTATIONS

Figure 2:
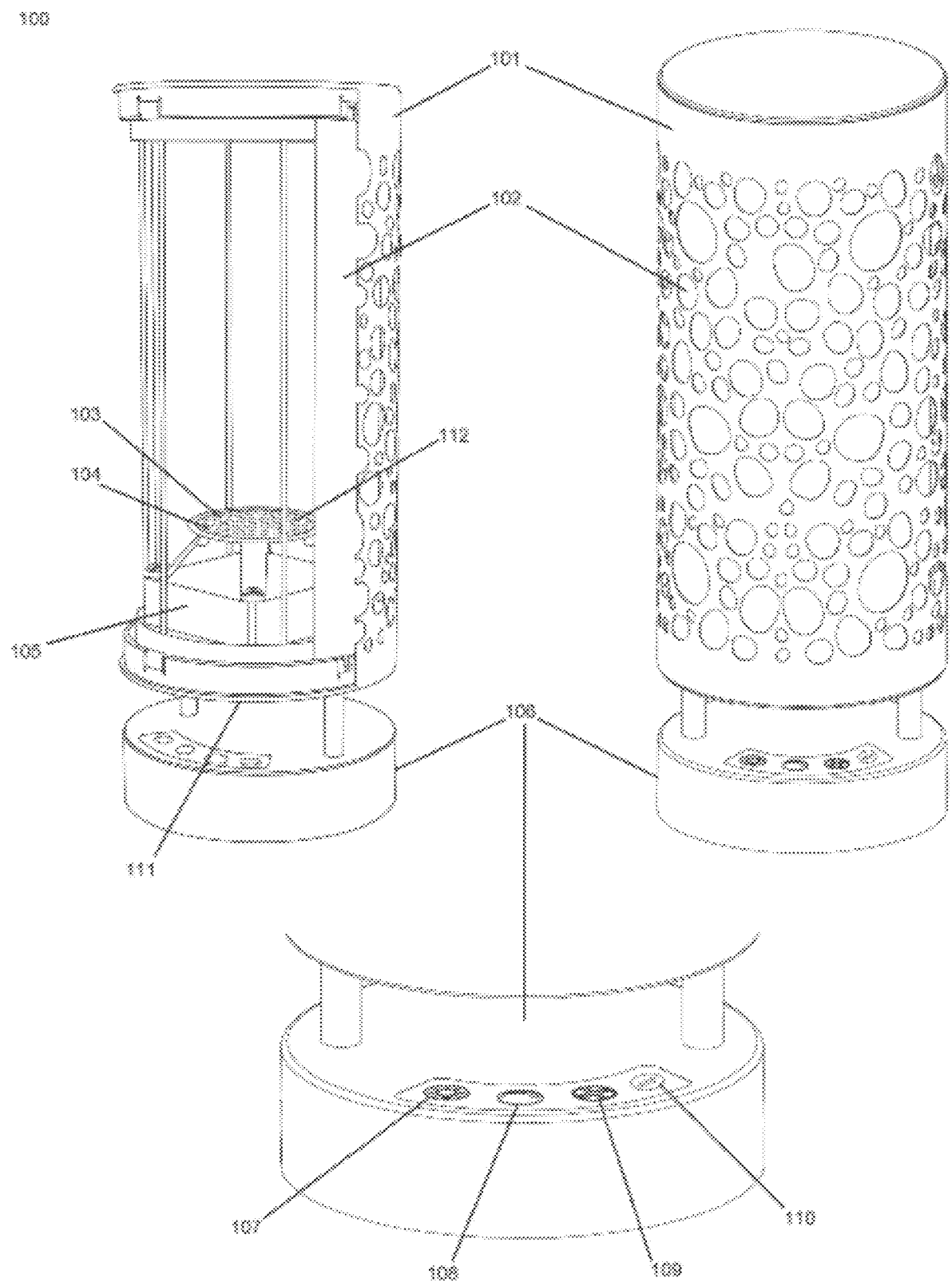
FIG. 2 schematically depicts an embodiment of the present disclosure in the form of a table lamp.

FIG. 2 is an embodiment of the lighting apparatus of the present disclosure in the form of a desktop lamp 100. The desktop lamp 200 has an external housing 101 to house an air filter 102, a fan 105, and three types of LEDs: 3000K white LEDs 104 (brown dots), 5000K white LEDs 103 (yellow dots), and broad-band near-IR LEDs 112 (black dots). The controller is hidden inside the base 106 and is configured to provide various functions: color selection (via touch button 107), dimming mode operation (via touch button 108), fan operation 109 (via touch button 109), and 40 Hz strobing operation (via touch button 110).

With this table lamp embodiment, the visible light sources (3000K white LEDs 104, or 5000K white LEDs 103, or both) always emit a radiation energy higher than the radiation energy emitted by the near-IR LEDs 112.

Figure 1:
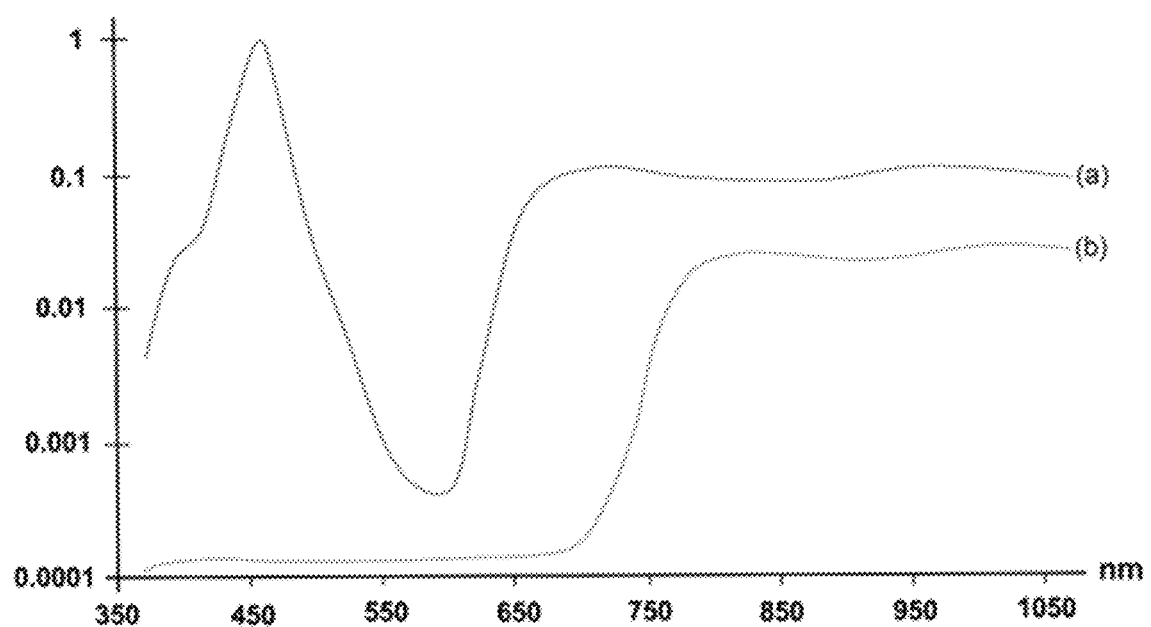
FIG. 1 schematically depicts the SPD of a near-IR LED light source before (a) and after (b) the use of a high-pass filter.

3000K white LEDs 104 and 5000K white LEDs 103 emit no wavelengths in the 700 nm to 1400 nm wavelength range. The near-IR LEDs 112 have an SPD as shown in FIG. 1(b), i.e., the near-IR LEDs 112 emit almost no visible wavelengths. Moreover, the near-IR LEDs 112 have a smooth (i.e., non-peaked), continuous SPD between 750 nm to 1050 nm wavelength range. If using a near-IR LED emitting visible wavelengths, then it would be necessary to use an optical high-pass filter with a cutoff wavelength around 750 nm to filter out the visible wavelengths. The controller of the embodiment 100 is configured to set the radiation energy emitted by the near-IR LEDs 112 in the 700 nm to 1400 nm wavelength range to be around 25% of the radiation energy emitted by 3000K white LEDs 104 and 5000K white LEDs 103 in the 380 nm to 700 nm wavelength range, So the radiation energy emitted by the near-IR LEDs 112 in the 700 nm to 1400 nm wavelength range is high even for stimulating a human subject and at the same time low enough as not to result in near-IR radiation overdosage.

The dimming button 108 supports five dimming modes (where visible light includes 3000K white LEDs 104 and 5000K white LEDs 103)

Mode 1: visible light on at 1000 lm, and the near-IR LEDs 112 on at 100%.

Mode 2: visible light on at 1000 lm, and the near-IR LEDs 112 off.

Mode 3: visible light on at 500 lm, and the near-IR LEDs 112 on at 50%.

Mode 4: visible light on at 500 lm, and the near-IR LEDs 112 off.

Mode 5: visible light off and the near-IR LEDs 112 off.

Modes 2 and 4 are non-near-IR modes for the near-IR LEDs 112 are off under these two modes.

The color selection button 107 is used to set the color temperature of the lamp. There are three color temperature modes under normal operation when the dimming button 108 is set to Mode 1 or 2 (i.e., at 100% dimming level):

Color Warm: only 3000K white LEDs 104 are turned on generating 1000 lm.

Color Medium: 3000K white LEDs 104 and 5000K white LEDs 103 are mixed to create 4000K light, generating 1000 lm.

Color Cold: only 5000K white LEDs 103 are turned on generating 1000 lm.

In the Color Medium mode, the controller performs a color temperature fusion of the 3000K LEDs and the 5000K LEDs with 50% light output from each, thus each contributes 500 lm light output.

If the dimming button 108 is set to Mode 3 or 4 (i.e., at 50% dimming level), then:

Color Warm: only 3000K white LEDs 104 are turned on generating 500 lm.

Color Medium: 3000K white LEDs 104 and 5000K white LEDs 103 are mixed to create 4000K light, generating 500 lm.

Color Cold: only 5000K white LEDs 103 are turned on generating 500 lm.

In the Color Medium mode, the controller performs a color temperature fusion of the 3000K LEDs and the 5000K LEDs with 50% light output from each, thus each contributes 250 lm light output.

There are two approaches to implement the 40 Hz strobing operation for the embodiment 100 for Alzheimer's treatment: amplitude modulation and color temperature fusion. When implemented 40 Hz strobing with amplitude modulation depth percentage at 20%, three color temperature modes would operate as follows assuming the dimming button 108 is set to Mode 1 or 2 (i.e., at 100% dimming level):

Color Warm: 3000K white LEDs 104 strobe between 800 lm and 1000 lm at 40 Hz.

Color Medium: 3000K white LEDs 104 and 5000K white LEDs 103 both strobe between 400 lm and 500 lm at 40 Hz, resulting a total light output strobing between 800 lm and 1000 lm at 4000K.

Color Cold: 5000K white LEDs 103 strobe between 800 lm and 1000 lm at 40 Hz.

Similarly, if the dimming button 108 is set to Mode 3 or 4 (i.e., at 50% dimming level), then:

Color Warm: 3000K white LEDs 104 strobe between 400 lm and 5000 lm at 40 Hz.

Color Medium: 3000K white LEDs 104 and 5000K white LEDs 103 both strobe between 200 lm and 250 lm at 40 Hz, resulting a total light output strobing between 400 lm and 500 lm at 4000K.

Color Cold: 5000K white LEDs 103 strobe between 400 lm and 5000 lm at 40 Hz.

Alternatively, the 40 Hz strobing operation for Alzheimer's treatment may be implemented via color temperature fusion. With color temperature fusion, three color temperature modes would operate as follows assuming the dimming button 108 is set to Mode 1 or 2 (i.e., at 100% dimming level, with a total light output of 1000 lm):

Color Warm: strobing between 3000K and 3200K color temperatures (both at 1000 lm) at 40 Hz for creating a blended light at 3100K, wherein 3200K color temperature is created by mixing 90% 3000K LEDs light output (i.e., at 900 lm) and 10% 5000K LEDs light output (i.e., at 100 lm).

Color Medium: strobing between 3900K and 4100K color temperatures at 40 Hz for creating a blended light at 4000K, wherein 3900K temperature is created by mixing 55% 3000K LEDs light output (i.e., at 550 lm) and 45% 5000K LEDs light output (i.e., at 450 lm), and 4100K color temperature is create by mixing 45% 3000K LEDs light output (i.e., at 450 lm) and 55% 5000K LEDs light output (i.e., at 550 lm).

Color Cold: strobing between 4800K and 5000K color temperatures at 40 Hz for creating a blended light at 4900K, wherein 4800K color temperature is created by mixing 10% 3000K LEDs light output (i.e., at 100 lm) and 90% 5000K LEDs light output (i.e., at 900 lm).

Similarly, if the dimming button 108 is set to Mode 3 or 4 (i.e., at 50% dimming level, with a total light output of 500 lm), then:

Color Warm: strobing between 3000K and 3200K color temperatures (both at 500 lm) at 40 Hz for creating a blended light at 3100K, wherein 3200K color temperature is created by mixing 90% 3000K LEDs light output (i.e., at 450 lm) and 10% 5000K LEDs light output (i.e., at 50 lm).

Color Medium: strobing between 3900K and 4100K color temperatures at 40 Hz for creating a blended light at 4000K, wherein 3900K temperature is created by mixing 55% 3000K LEDs light output (i.e., at 275 lm) and 45% 5000K LEDs light output (i.e., at 225 lm), and 4100K color temperature is create by mixing 45% 3000K LEDs light output (i.e., at 225 lm) and 55% 5000K LEDs light output (i.e., at 275 lm).

Color Cold: strobing between 4800K and 5000K color temperatures at 40 Hz for creating a blended light at 4900K, wherein 4800K color temperature is created by mixing 10% 3000K LEDs light output (i.e., at 50 lm) and 90% 5000K LEDs light output (i.e., at 450 lm).

ADDITIONAL AND ALTERNATIVE IMPLEMENTATION NOTES

Although the techniques have been described in language specific to certain applications, it is to be understood that the appended claims are not necessarily limited to the specific features or applications described herein. Rather, the specific features and examples are disclosed as non-limiting exemplary forms of implementing such techniques.

As used in this application, the term "or" is intended to mean an inclusive "or" rather than an exclusive "or." That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more," unless specified otherwise or clear from context to be directed to a singular form.

What is claimed is:

1. A lighting apparatus, comprising:
   a first visible light source configured to emit a light with a first color temperature between 1900K and 6800K;
   a near-infrared (near-IR) radiation source configured to emit a wavelength in a 700 nm to 1400 nm wavelength range, wherein:
      the near-IR radiation source is further configured to emit a 300 nm continuous spectral range of emission between 700 nm and 1400 nm, and
      the spectral range is a smooth, non-peaked spectral power distribution (SPD) between 700 nm and 1400 nm,
   a controller, wherein:
      the controller is configured to convert an external alternating-current (AC) mains power to a first internal power to drive the first visible light source,
      the controller is configured to convert the external AC mains power to a second internal power, different from the first internal power, to drive the near-IR radiation source, and
      the controller is configured to set a radiation energy emitted by the lighting apparatus in the 700 nm to 1400 nm wavelength range to be less than the radiation energy emitted by the lighting apparatus which is in a 380 nm to 700 nm wavelength range.

2. The lighting apparatus of claim 1, wherein the controller is configured to set the radiation energy emitted by the lighting apparatus in the 700 nm to 1400 nm wavelength range to be greater than 10% of the radiation energy emitted by the lighting apparatus in the 380 nm to 700 nm wavelength range.

3. The lighting apparatus of claim 1, wherein the controller is configured to operate the lighting apparatus in a non-near-IR mode by turning on the first visible light source but not the near-IR radiation source.

4. The lighting apparatus of claim 1, wherein the first visible light source comprises a light emitting diode (LED).

5. The lighting apparatus of claim 1, wherein the near-IR radiation source comprises a light emitting diode (LED).

6. The lighting apparatus of claim 1, wherein the near-IR radiation source comprises a filament radiation source.

7. The lighting apparatus of claim 1, wherein the near-IR radiation source comprises a filament light emitting diode (LED).

8. The lighting apparatus of claim 1, further comprising an optical high-pass filter with a cutoff wavelength between 700 nm and 800 nm, wherein the optical high-pass filter is configured to attenuate visible wavelengths emitted by the near-IR radiation source.

9. The lighting apparatus of claim 1, wherein the controller is configured to strobe the first visible light source with a strobing frequency between 35 Hz and 45 Hz via amplitude modulation on the light emitted by the first visible light source.

10. The lighting apparatus of claim 9, wherein the controller is configured to modulate an amplitude modulation depth percentage on the light emitted by the first visible light source to be less than 50%.

11. The lighting apparatus of claim 9, wherein the controller is configured to support an adjustable amplitude modulation depth percentage on the light emitted by the first light source.

12. The lighting apparatus of claim 9, wherein the controller is configured to dim the light emitted by the first visible light source while maintaining a same amplitude modulation depth percentage.

13. The lighting apparatus of claim 1, wherein the first visible light source is configured to output more than one color temperature.

14. The lighting apparatus of claim 13, wherein the controller is configured to tune the first visible light source from one color temperature to another color temperature while maintaining a same amplitude modulation depth percentage.

15. The lighting apparatus of claim 9, wherein the controller is configured to tune the first visible light source from one color temperature to another color temperature while maintaining a same amplitude modulation depth percentage.

16. The lighting apparatus of claim 1, wherein the first visible light source further comprises a second visible light source with a second color temperature and a third visible light source with a third color temperature, different from the second color temperature.

17. The lighting apparatus of claim 16, wherein the controller is configured to strobe between a first linear combination of the second color temperature and the third color temperature and a second, different linear combination of the second color temperature and the third color temperature at a strobing frequency between 35 Hz and 45 Hz while maintaining a same light output by the lighting apparatus during strobing.

* * * * *